United States Patent
Bilby (10) Patent No.: US 9,951,672 B2
(45) Date of Patent: *Apr. 24, 2018

(54) METHOD AND SYSTEM FOR EXHAUST PARTICULATE MATTER SENSING

(71) Applicant: Ford Global Technologies, LLC, Dearborn, MI (US)

(72) Inventor: David Bilby, Auburn Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 239 days.

This patent is subject to a terminal disclaimer.

(21) Appl. No.: 14/937,632

(22) Filed: Nov. 10, 2015

(65) Prior Publication Data

US 2017/0130636 A1   May 11, 2017

(51) Int. Cl.

| | | |
|---|---|---|
| G01M 15/10 | (2006.01) | |
| F01N 9/00 | (2006.01) | |
| F01N 3/023 | (2006.01) | |
| F01N 11/00 | (2006.01) | |
| F01N 3/021 | (2006.01) | |
| G01N 15/00 | (2006.01) | |

(52) U.S. Cl.
CPC ............ *F01N 9/002* (2013.01); *F01N 3/021* (2013.01); *F01N 3/023* (2013.01); *F01N 11/00* (2013.01); *G01N 15/00* (2013.01); *F01N 2550/04* (2013.01); *F01N 2560/05* (2013.01); *F01N 2570/10* (2013.01)

(58) Field of Classification Search
USPC .............................. 73/114.69, 114.71, 114.75
See application file for complete search history.

(56) References Cited

U.S. PATENT DOCUMENTS

| | | | | |
|---|---|---|---|---|
| 7,543,477 B2* | 6/2009 | Berger | ............... | G01N 15/0656 73/23.33 |
| 7,963,106 B2 | 6/2011 | Schmidt et al. | | |
| 8,035,404 B2* | 10/2011 | Schnell | ............. | G01N 15/0656 324/71.4 |
| 8,310,249 B2* | 11/2012 | Paterson | ............. | F02D 41/1466 324/693 |

(Continued)

OTHER PUBLICATIONS

Zhang, Xiaogang, "Method and System For Exhaust Particulate Matter Sensing," U.S. Appl. No. 14/835,270, filed Aug. 25, 2015, 50 pages.

(Continued)

*Primary Examiner* — Eric S McCall
(74) *Attorney, Agent, or Firm* — Julia Voutyras; McCoy Russell LLP (57) ABSTRACT

Methods and systems are provided for sensing particulate matter by a particulate matter sensor positioned downstream of a diesel particulate filter in an exhaust system. In one example, a method may include accumulating incoming particulate matter by applying a higher bias to a first trap of the particulate matter sensor, and further charging the particulate matter and forming highly charged dendrites. The method further includes capturing the dendrites exiting the first trap by applying a lower bias to a second trap also housed within the same particulate matter sensor, thereby reducing the effects of exhaust flow rate on the particulate matter sensor and further increasing the sensitivity of the particulate matter sensor.

20 Claims, 7 Drawing Sheets

(56) References Cited

U.S. PATENT DOCUMENTS

| | | | |
|---|---|---|---|
| 8,713,991 B2 | 5/2014 | Allmendinger et al. | |
| 8,823,401 B2* | 9/2014 | Roth | G01N 15/0656 324/699 |
| 2012/0151992 A1* | 6/2012 | Harada | G01N 15/0656 73/23.33 |
| 2012/0312074 A1* | 12/2012 | Allmendinger | G01N 1/2252 73/23.31 |
| 2013/0000280 A1 | 1/2013 | Korenev | |
| 2014/0174410 A1 | 6/2014 | Myers et al. | |
| 2016/0223432 A1* | 8/2016 | Kubinski | F01N 3/027 |
| 2016/0320285 A1* | 11/2016 | Weber | G01N 15/0656 |
| 2017/0058748 A1* | 3/2017 | Zhang | G01N 15/0656 |
| 2017/0067813 A1* | 3/2017 | Zhang | G01M 15/102 |

OTHER PUBLICATIONS

Zhang, Xiaogang, "System for Sensing Particulate Matter," U.S. Appl. No. 14/960,408, filed Dec. 11, 2015, 40 pages.

Kubinski, David John, "Method and System for Exhaust Particulate Matter Sensing," U.S. Appl. No. 14/613,012, filed Feb. 3, 2015, 56 pages.

* cited by examiner

METHOD AND SYSTEM FOR EXHAUST PARTICULATE MATTER SENSING

FIELD

The present description relates generally to the design and use of particle matter (PM) sensors in an exhaust gas flow.

BACKGROUND/SUMMARY

Diesel combustion may generate emissions, including particulate matter (PM). The particulate matter may include diesel soot and aerosols such as ash particulates, metallic abrasion particles, sulfates, and silicates. When released into the atmosphere, PM can take the form of individual particles or chain aggregates, with most in the invisible sub-micrometer range of 100 nanometers. Various technologies have been developed for identifying and filtering out exhaust PMs before the exhaust is released to the atmosphere.

As an example, PM or soot sensors may be used in vehicles having internal combustion engines. A PM sensor may be located upstream and/or downstream of a diesel particulate filter (DPP), and may be used to sense PM loading on the filter and diagnose operation of the DPF. Resistive PM sensors may include interdigitated electrodes that sense a particulate matter or soot load based on a correlation between a measured change in electrical conductivity (or resistivity) between a pair of electrodes placed on a planar substrate surface of the sensor with the amount of PM deposited between the measuring electrodes. Specifically, the measured conductivity provides a measure of soot accumulation. However, resistive sensors may not deliver real-time measurement of soot, as there may be extended times while the sensor is just accumulating soot during which the sensor may not provide any real-time signal at all.

An example attempt to address this issue is shown in U.S. Pat. No. 8,713,991 where a real-time sensor, such as a high voltage PM sensor, is used. Therein, the high voltage PM sensor includes a single pair of electrodes and accumulates soot due to electrostatic capture similar to the resistive soot; however, in this case, soot begins to aggregate due to the strong electric field applied between the electrodes. When the soot aggregates break off the electrode, they carry part of the charge of the electrode with them and deposit their charge when they contact a grounded part of the sensor or the exhaust system. This charge deposition on the grounded part of the sensor may be detected as a current pulse flowing between the electrode and ground.

However, the inventors herein have recognized potential issues with such systems. As one example, the sensitivity of the high voltage sensor may change abruptly when there is any abrupt change in exhaust flow rate causing transients in the measured current. The flow of the soot aggregates towards the grounded part of the sensor may depend on the exhaust flow rate, for example. As such, an increased exhaust flow may result in a decrease in the amount of aggregates falling onto the grounded thereby causing a drop in the measured current. Likewise, a decreased exhaust flow rate may increase the amount of aggregates reaching the ground, thereby causing a spike in the measured current. Due to these current transients in the sensor output, the sensor capturing soot exiting the DPF may not truly reflect the DPF filtering capabilities.

In one example, the issues described above may be partially addressed by a method comprising collecting and charging particulate matter (PM) in an exhaust entering a PM sensor by applying a first voltage only to a first set of electrodes housed within the PM sensor, and measuring the charged PM by applying a second voltage only to a second set of electrodes housed within the PM sensor further separated from the first set of electrodes by a distance, the first voltage being higher than the second voltage. In this way, by juxtaposing two sets of electrodes within the same PM sensor housing, the second set of electrodes may be used for detecting the PMs in the exhaust. Aggregates exiting the first set of electrodes may be captured by the second set of electrodes, thereby reducing current transients in the second set of electrodes. Thus sensitivity to the sensor output on exhaust flow rate may be reduced and the sensor output may begin to more closely measure the DPF filtering capabilities more accurately and reliably in real-time.

As one example, by using the first set of electrodes primarily for charging the soot and the second set of electrodes primarily for measuring the highly charged soot, any transients in the measured current in the second set of electrodes may be reduced. In this way, by juxtaposing the second set of electrodes with the first set of electrodes, the charged soot exiting the first set of electrodes may be captured by the second set of electrodes thereby rendering the sensor more independent of the exhaust flow rate. Overall, these characteristics of the sensor may cause an output of the PM sensor to be more accurate, thereby increasing the accuracy of estimating particulate loading on a particulate filter.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
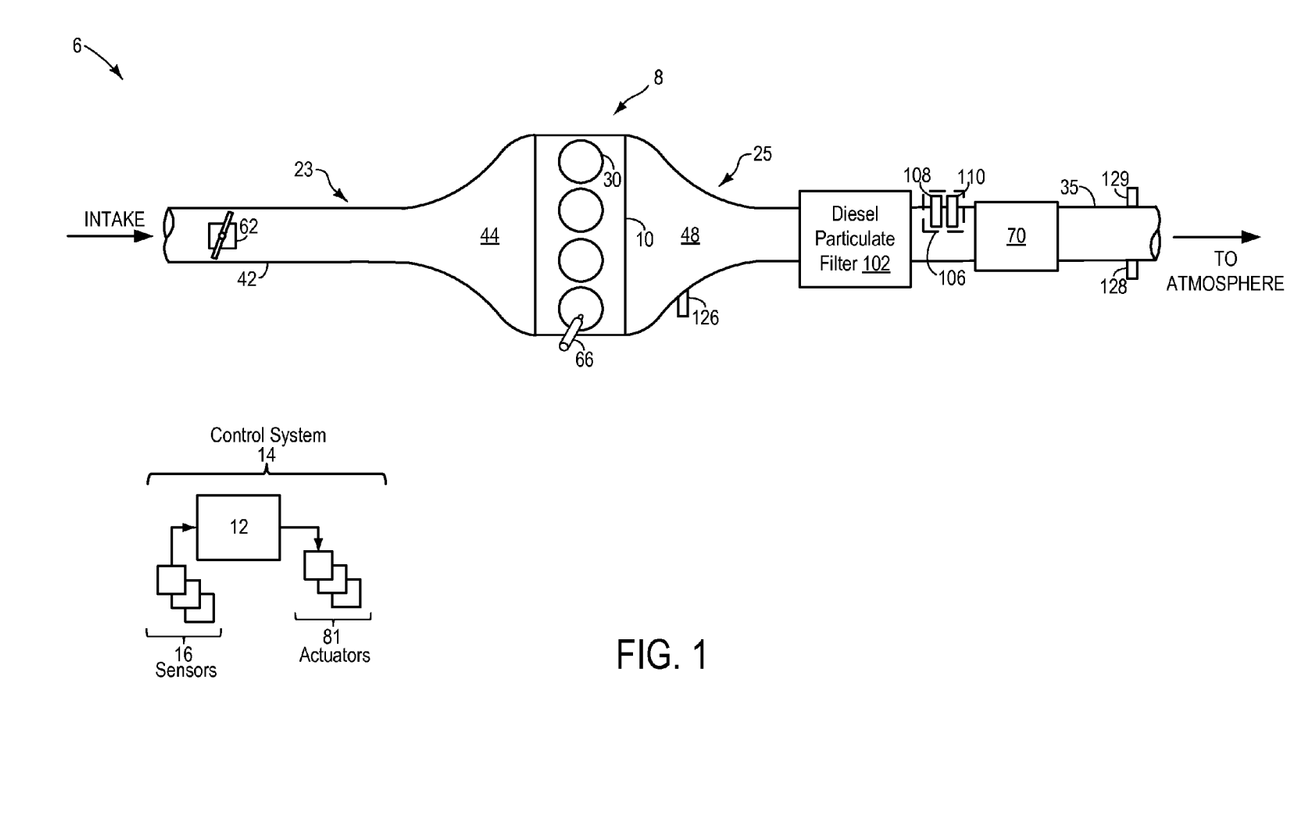
FIG. 1 shows a schematic diagram of an engine and an associated particulate matter (PM) sensor positioned in an exhaust flow.
Figure 2:
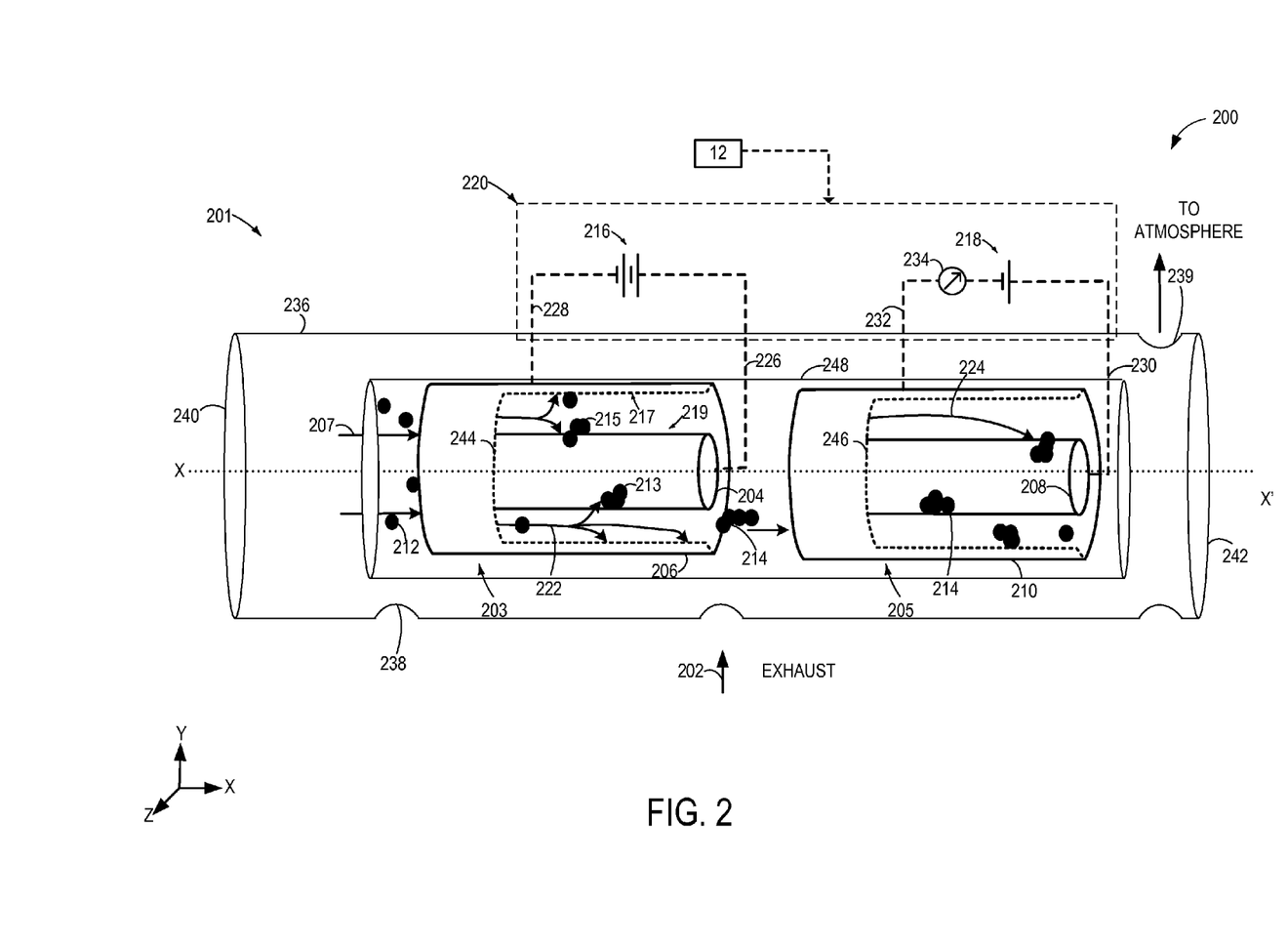
FIG. 2 shows a first example embodiment of the PM sensor including two traps, each including a pair of cylindrical electrodes separated from one another by a gap.
Figure 3:
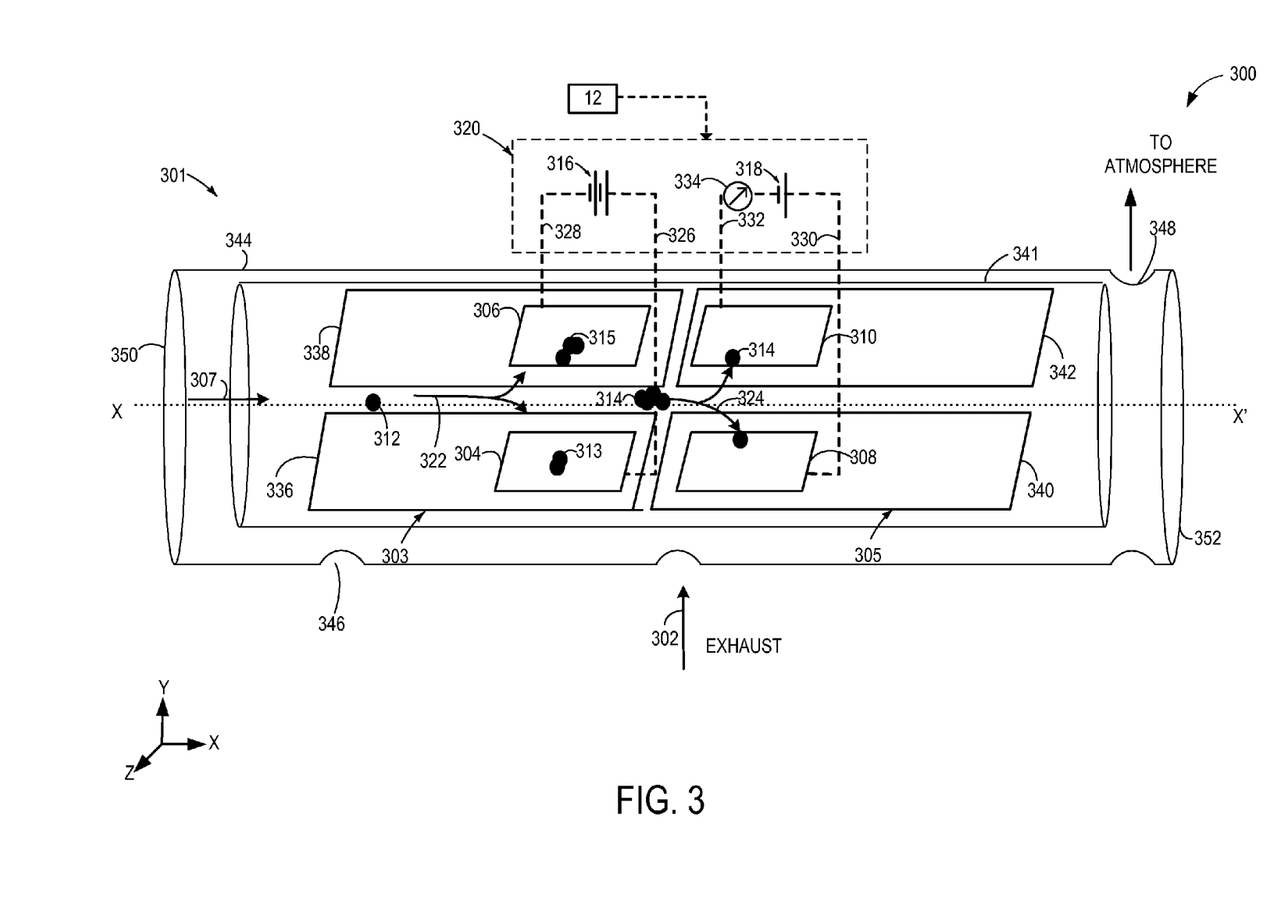
FIG. 3 shows a second example embodiment of the PM sensor where the two traps each include a pair of planar continuous electrodes further separated from one another.

The following description relates to sensing particulate matter (PM) in an exhaust flow of an engine system, such as the engine system shown in FIG. 1. A PM sensor placed in an exhaust passage of the engine system may include two traps separated from one another by a gap. PM entering the PM sensor may accumulate and get charged by the first trap operated at a higher voltage and may form aggregates. The aggregates may separate from and exit the first trap and subsequently enter the second trap wherein they may be captured by the second trap operated at a lower voltage. Example embodiments of the PM sensor are shown in FIGS. 2 and 3. A controller may be configured to perform a control routine, such as the routine of FIG. 3 to measure the PM load on the sensor based on a current measured across the second trap. In addition, the controller may intermittently clean the traps (as shown in the method presented at FIG. 5) to enable continued PM detection and perform diagnostics on a particulate filter positioned upstream of the PM sensor based on an output of the PM sensor (as shown in the method presented at FIG. 6). An example relation between the voltages applied to the traps and amount of PM ejected downstream of the PM sensor is depicted with reference to FIG. 7. In this way, by juxtaposing the two traps within the PM sensor housing, charged PM exiting the first trap may be captured by the second set of electrodes (in one example the charged PM exiting the first trap are captured almost instantaneously by the second set of electrodes). Thus, the sensor output may become more independent (e.g., fully independent) of the exhaust flow rate. Overall, the ability of the PM sensor to estimate the filtering capabilities of the DPF (and thereby to detect DPF leaks) may be improved and exhaust emissions compliance may be improved as PMs in the exhaust may be detected more accurately and reliably.

Turning now to FIG. 1, a schematic depiction of a vehicle system 6 is shown. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in a PM sensor 106 and further processed in emission control device 70 and expelled to the atmosphere via exhaust passage 35. In the depicted example, PM sensor 106 may include traps 108 and 110 and may estimate the filtering efficiency of the DPF 102 based on a current measured across one of the traps of the PM sensor, for example. Schematic views 200 and 300 of the PM sensor 106 are shown at FIGS. 2 and 3, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. For example, the controller 12 may control switches (not shown) in the PM sensor detection circuitry and further control voltage supplies in the circuitry. Example routines are described herein with reference to FIGS. 4-6.

Turning now to FIG. 2, a schematic view 200 of a first example embodiment of a particulate matter (PM) sensor 201 (such as PM sensor 106 of FIG. 1) is shown. The PM sensor 201 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1).

FIG. 2 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example.

Schematic view 200 shows PM sensor 201 inside exhaust passage with exhaust gases flowing from downstream of a diesel particulate filter towards an exhaust tailpipe, as indicated by arrow 202. PM sensor 201 may comprise a cylindrical tube (protection tube) 236 that may serve to protect the sensor and the electrical elements of the sensor that are housed within and additionally may serve to redirect and optimize the gas flow over them. A plurality of holes 238, 239 (or pores) may be configured along the surface of cylindrical tube 236 for enabling flow-through of exhaust gas. Exhaust gas may enter the PM sensor 201 through the plurality of holes 238 (three holes shown as a non-limiting example) on the upstream side of the cylindrical tube 236 closer to the DPF as indicated by arrow 202. The exhaust may then flow through conduits and flow paths (not shown) such that the exhaust may then enter a first trap 203 and subsequently enter a second trap 205 where the PMs may be detected, and the undetected PMs in the exhaust may exit the PM sensor 201 (to atmosphere) on the downstream side, through the plurality of holes 239 (one hole shown as a non-limiting example). Additionally, exhaust gas may enter and exit the PM sensor assembly though the base 242 of the cylindrical tube 236 that is positioned inside the exhaust passage. In this way, exhaust gas may enter the cylindrical tube in a direction substantially orthogonal to the direction of exhaust flow. The cylindrical tube 236 of the PM sensor 201 may be mounted directly onto exhaust passage such that the central axis X-X' may be perpendicular to the direction of exhaust flow as indicated by arrow 202. The upper portion of the sensor body may be attached to the exhaust pipe such that the sensing portion of the PM sensor comprising the traps may be extended into the exhaust pipe. As such, the cylindrical tube 236 of the PM sensor 201 may define an enclosed volume within which the traps are housed. A top surface 240 of the cylindrical tube 236 may be mounted onto the exhaust pipe, and a bottom surface 242 of the cylindrical tube 236 may be extended into the exhaust pipe.

The traps 203 and 205 may be non-limiting examples of traps 108 and 110 shown in FIG. 1. The first trap 203 (also referred to a high voltage (HV) trap) may include a first set of electrodes 204 and 206 separated by a distance. As such, the electrode 206 may be hollow and cylindrical in shape, and further surround the second cylindrical electrode 204 while the cylindrical electrode 204 may be solid throughout. The cylindrical electrode 204 is of smaller diameter than the cylindrical electrode 206 and may fit completely inside the electrode 206. These electrodes may be typically manufactured from metals such as platinum, gold, osmium, rhodium, iridium, ruthenium, aluminum, titanium, zirconium, and the like. In some examples, the electrodes may be formed by depositing a uniform layer of metal onto a substrate (not shown) of highly electrically insulating materials. As such, the electrode surface may be continuous and not interdigitated.

The electrode 204 (also referred to as the positive electrode) of the first trap 203 may be connected to a positive terminal of a voltage source 216 via a connecting wire 226. Similarly, the electrode 206 (also referred to as the negative electrode) of the first trap may be connected to a negative terminal of the same voltage source 216 via a connecting wire 228. In some embodiments, a switch (not shown) may be included and a controller (such as controller 12 of FIG. 1) may control the switch to selectively connect and disconnect the electrodes from the voltage source 216. The electrical connections 226, and 228, the voltage source 216 may be part of an electric circuit 220 that may be housed outside the exhaust passage (as one example, <1 meter away).

Juxtaposed next to the first trap 203 and further separated from the first trap by a distance is a second trap 205. For example, the distance may include a space with no components there-between. As such, the second trap 205 (also referred to a low voltage (LV) trap) may also be housed within the same PM sensor 201. The traps may be arranged inside the PM sensor 201 such that the axes of the cylindrical electrodes are along and parallel to the axis X-X' of the PM sensor itself. Similar to the first trap, the second trap 205 also includes a second set of electrodes comprising two cylindrical electrodes 208 and 210 separated by a distance. The details of the cylindrical electrodes 208 and 210 may be similar to the cylindrical electrodes 204 and 206. In some examples, the first trap and the second trap may be identical and sharing all features. In other examples, the first trap may be different from the second trap, and may share some common features.

Briefly, the cylindrical electrode 210 may be hollow and further surround the cylindrical electrode 208 while the cylindrical electrode 208 may be solid throughout. The cylindrical electrode 208 is of smaller diameter than the cylindrical electrode 210. These electrodes may be typically manufactured from metals and in some examples, the electrodes may be formed by depositing a uniform layer of metal onto a substrate (not shown) of highly electrically insulating materials. As such, the electrode surface may be continuous and not interdigitated.

The electrode 208 (also referred to as the positive electrode) of the second trap 205 may be connected to a positive terminal of a voltage source 218 via a connecting wire 230. Similarly, the electrode 210 (also referred to as the negative electrode) of the second trap may be connected to a measurement device 234 and then to a negative terminal of the same voltage source 218 via a connecting wire 232. As such a measurement device may not be connected to the first trap 203 but only connected to the second trap 205. In some embodiments, a switch (not shown) may be included and a controller (such as controller 12 of FIG. 1) may control the switch to selectively connect and disconnect the electrodes from the voltage source.

The voltage source 218 may supply a lower voltage to the second trap 205 compared to the voltage supplied to the first trap 203. The voltage source 216 may be capable of supplying a voltage between 500 and 2000V, and the voltage source 218 may be capable of supplying a voltage between 1 and 500 V. As an example, the voltage source 218 may supply a lower voltage $V_L$ of about 10 V while the voltage source 216 may supply a higher voltage $V_H$ of about 1000 V. Thus, a uniform electric field may be generated between each of the electrodes of the first trap and the second trap that may function to attract and/or repel charged PM entering the traps. However, the strength of the electric field between the electrodes of the first trap may be larger than the electric field generated in the second trap. Herein, the voltage sources 216 and 218 may be controlled by a controller, such as controller 12 of FIG. 1, for example. These voltages are given as a reference point in a device with a 1 mm inter-electrode (the 206 to 204 gap or the 208 to 210 gap, for instance) spacing. Smaller voltages and inter-electrode gap may be used if the electric fields in the LV and HV traps are maintained.

In some examples, the first and the second traps may be regenerated. Regeneration of the traps may include increasing the temperature of a heating element embedded in the each of the traps of the sensor, until the soot load of the traps has been sufficiently reduced by oxidation of the carbon particles between the electrodes. A controller such as controller 12 of FIG. 1, may effect regeneration of the traps by actuating the heating element coupled thermally to the electrode surface as explained in detail with reference to FIG. 5.

Exhaust may enter the PM sensor 201 via holes 238 (as indicated by arrow 202), and may further travel along the conduits (not shown) arranged inside the PM sensor 201 such that the exhaust enters the first trap 203 as indicated by arrow 207. In some examples, the exhaust entering the first trap may be orthogonal to the flow of exhaust in the exhaust pipe (non-limiting example is shown in FIG. 2). In some more examples, the traps in the PM sensor may be arranged such that the exhaust entering the first trap may be parallel to the direction of flow of exhaust in the exhaust pipe, without deviating from the scope of the invention. Other arrangements of the traps within the PM sensor may also be envisioned where the exhaust may enter the first trap at other incident angles between 0° and 90° with respect to direction of exhaust flow inside the exhaust pipe.

As such, the PM sensor 201 may include an inner protection tube 248 that may serve to block exhaust from entering the second trap before entering the first trap, for example. In some examples, the PM sensor 201 may not include a protection tube 248, and additional conduits arranged inside the PM sensor may be direct the exhaust first into the first trap for charging the soot and subsequently into the second trap for measuring the charged soot exiting the first trap.

PMs or soot 212 in the exhaust are natively charged and may enter the first trap 203 and further enter the space between the positive electrode 204 and the negative electrode 206. When a voltage bias is applied between the electrodes of the first trap 203, a uniform electric field may be generated in the space between the electrodes of the first trap, for example. Due to the uniform electric field existing between the electrodes, charged PMs entering the first trap may experience electrostatic forces attracting them towards the electrodes of opposite polarity (indicated by arrow 222). For example, PMs carrying a small negative charge may be attracted towards the positive electrode 204 of the first trap, while the PMs carrying a small positive charge may be attracted towards the negative electrode 206 of the first trap. Herein, high voltage may be applied to the electrodes of the first trap via the voltage source 216, therefore a strong electric field may be generated between the electrodes of the first trap.

The first trap may begin to collect and accumulate the PMs entering the first trap. Soot grows into dendrite structures which are anchored onto the electrodes, having been driven there by electric forces as explained earlier. Herein, the PMs 212 entering the first trap 203 may begin to form aggregates 213 and 215 (also known as dendrites) on the surfaces of the electrodes of the first trap. Once the aggregates contact the surfaces of the electrodes, they may acquire the same polarity surface charge as the electrode surface.

For example, aggregate 213 collecting on an outer surface 219 of the positive electrode 204 may acquire a positive surface charge. Similarly, aggregates 215 forming on an inner surface 217 of the negative electrode 206 may acquire a negative surface charge. Herein, the size of the aggregates 213 and 215 may be larger than the size of incoming PMs 212. In order to aid in the visualization, a portion 244 of the negative electrode 206 is cut away to show aggregates accumulating on the inner surface of the negative electrode and the outer surface of the positive electrode.

At the electrode surfaces, the aggregates may experience weak intermolecular forces of attraction such as Van der Waals forces that keep the aggregates attached to the surfaces of the electrodes. In addition, due to the transfer of electric charges from the electrodes themselves, the aggregates may begin to possess increased surface charges. For example, aggregates 213 growing on the outer surface 219 of the positive electrode 204 may accumulate enough positive surface charge that the aggregates may now begin to experience electrostatic repulsion from the positive electrode itself. Similarly, aggregates 215 growing on the inner surface 217 of the negative electrode 206 may accumulate enough negative surface charge that the aggregates may now begin to experience electrostatic repulsion from the negative electrode. When the aggregates 214 reach a threshold size, then the surface charges may reach threshold charge levels such that the electrostatic repulsion from the electrode may begin to be stronger than the weak Van der Waals force attaching them to the electrode itself. The increased repulsive forces may cause the aggregates 214 (size of aggregates 214 may be larger than the aggregates 213, 215 and also incoming PMs 212, for example) to break free from the surfaces of the electrodes and flow out of the first trap. However, when breaking away from the electrodes of the first trap and exiting the first trap, the aggregates still possess their surface charge, however amplified. Thus, the first trap may be used only for accumulating and charging the incoming soot. Herein, the first trap may not be used to measure soot load on the PM sensor.

As explained earlier, a second trap 205 may be juxtaposed to the first trap. Herein, the second trap is positioned apart from the first trap with only space and no other components there-between. Exhaust flow may carry the aggregates 214 breaking off the electrodes of the first trap into the second trap. The voltage source 218 supplies a voltage lower than that supplied by the voltage source 216, for example. The second trap may additionally include a measurement device 234. Further, the voltage source 218 and the measurement device of the electrical circuit may be controlled by a controller, such as controller 12 of FIG. 1, so that particulate matter collected at the PM sensor may be used for diagnosing leaks in the DPF, for example. As such, the measurement device 234 may be any device capable of measuring electrical current across the electrodes of the second trap 205, such as an ammeter.

Similar to the first trap, a uniform electric field also exists between the electrodes of the second trap. However, the electric field in the second trap is normally, but not necessarily, weaker than the first trap, because of the typically lower voltage that is applied across the electrodes of the second trap. When the aggregates carrying large surface charges enter the second trap 205, they may be attracted quickly towards the electrodes of opposite polarity (as indicated by arrow 224). In contrast to the first trap, soot collected in the lower electric field of the second trap will not experience strong repulsive forces which cause aggregate break off.

For example, positively charged aggregates exiting the first trap may experience an attraction towards the negative electrode 210 of the second trap. Similarly, negatively charged aggregates exiting the first trap may be attracted towards the positive electrode 208 of the second trap. As the aggregates 214 get deposited between the positive electrode 208 and the negative electrode 210, causing an increase in the current measured by the measurement device 234. In some examples, since the charge of the aggregates in increased, the current measured by the measurement device 234 may also be amplified. The controller, such as controller 12 of FIG. 1, may be able to use the current measured by the measurement device 234 and infer a corresponding PM or soot load on the second trap 205 of the PM sensor 201. As such, the second trap 205 may be primarily used only for measuring the soot load on the PM sensor 201 and not for charging the soot, for example. In some examples, the aggregates exiting the first trap and entering the second trap may possess increased surface charges, as a result, larger currents may be detected by the measurement device 234. As a result, the detection circuitry may be simplified, and additional amplifiers may not be required. The technical effect of placing the second trap right next to the first trap is that all of the aggregates escaping out of the first trap may be captured by the second trap, thereby increasing the soot load estimation efficiency of the PM sensor.

Thus, by applying a higher electric field between a first pair of electrodes of the first trap of the PM sensor PM entering the first trap may begin to form aggregates (or dendrites). When these aggregates break off, they may enter the second pair of electrodes where the soot load of the PM sensor may be measured. As such, a lower electric field is applied between the second set of electrodes of the second trap, charged aggregates may be captured. In some examples, amplified currents may be registered in the measuring device. In this way, by using the second pair of electrodes to capture the aggregates, any transients (peaks or valleys) in measured current may be reduced.

Turning now to FIG. 3, a schematic view 300 of a second example embodiment of a particulate matter (PM) sensor 301 (such as PM sensor 106 of FIG. 1) is shown. The PM sensor 301 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1). Herein, two sets of planar parallel electrodes may be positioned inside the PM sensor. If shown directly contacting each other, or directly coupled, then such elements may be referred to as directly contacting or directly coupled, respectively, at least in one example.

The PM sensor 301 may be an example of PM sensor 201 of FIG. 2 and further include all the features described with reference to PM sensor 201. Herein, an example configuration of the PM sensor including planar geometries is shown.

FIG. 3 shows an example configuration with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

Schematic view 300 shows PM sensor 301 inside exhaust passage with exhaust gases flowing from downstream of a diesel particulate filter towards an exhaust tailpipe, as indicated by arrow 302. Similar to PM sensor 201, PM sensor 301 may comprise a cylindrical tube (protection tube) 244 that may serve to protect the electrical elements of the sensor components that are housed within and additionally may serve to redirect and optimize the gas flow over them. In some examples, the protection tube may be rectangular in shape. A plurality of holes 346, 348 (or pores) may be configured along the surface of cylindrical tube 344 for enabling flow-through of exhaust gas. Exhaust gas may enter the PM sensor 301 through the plurality of holes 346 (three holes shown as a non-limiting example) on the upstream side of the cylindrical tube 344 closer to the DPF as indicated by arrow 302. The exhaust may then flow through conduits and flow paths (not shown) such that the exhaust may then enter a first trap 303 and subsequently enter a second trap 305 where the PMs may be detected, and the undetected PMs in the exhaust may exit the PM sensor 301 (to atmosphere) on the downstream side, though plurality of holes 348 (two holes shown as a non-limiting example). The cylindrical tube 344 of the PM sensor 301 may be mounted directly onto exhaust passage such that the central axis X-X' may be perpendicular to the direction of exhaust flow as indicated by arrow 302. As such, the cylindrical tube 344 of the PM sensor 301 may define an enclosed volume within which the traps are housed. A top surface 350 of the cylindrical tube 344 may be mounted onto the exhaust pipe, and a bottom surface 352 of the cylindrical tube 344 may be extended into the exhaust pipe.

The traps 303 and 305 may be non-limiting examples of traps 108 and 110 shown in FIG. 1. The first trap 303 (also referred to a high voltage (HV) trap) may include a first set of electrodes 304 and 306 separated by a distance. The electrodes 304 and 306 may be planar electrodes. As such, the electrode surface may be continuous and uniform and not interdigitated. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 304 and 306 are formed on substrates 336 and 338 respectively. The substrates 336 and 338 may be manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for electrodes. Herein, the electrode 304 may be formed on a surface of the substrate 336, and similarly, the electrode 306 may be formed on a surface of the substrate 338. The electrodes may be positioned inside the PM sensor 301 such that the electrodes 304 and 306 face one another and are parallel to one another and further separated from each other by a distance. The electrodes 304 and 306 may cover a portion of the substrate surfaces 336 and 338 respectively. In some examples, the electrodes 304 and 306 may cover the entire length of the substrate surfaces 336 and 338 respectively.

The electrode 304 (also referred to as the positive electrode) of the first trap 303 may be connected to a positive terminal of a voltage source 316 via a connecting wire 326. Similarly, the electrode 306 (also referred to as the negative electrode) of the first trap may be connected to a negative terminal of the same voltage source 316 via a connecting wire 328. In some embodiments, a switch (not shown) may be included and a controller (such as controller 12 of FIG. 1) may control the switch to selectively connect and disconnect the electrodes from the voltage source. The electrical connections 326, and 328, the voltage source 316 may be part of an electric circuit that may be housed outside the exhaust passage (as one example, <1 meter away).

Juxtaposed next to the first trap 303 and further separated from the first trap by a distance is a second trap 305. For example, the distance may include a space with no components there-between. As such, the second trap 305 (also referred to a low voltage (LV) trap) may also be housed within the same PM sensor 301. The traps may be arranged inside the PM sensor 301 such that positive electrode 304 faces the negative electrode 306. Similar to the first trap 303, the second trap 305 also includes a second set of electrodes comprising two planar electrodes 308 and 310 formed on substrates 342 and 340 respectively, and parallel to one another and further separated from one another by a distance. In some examples, the first trap and the second trap may be identical and sharing all features. In other examples, the first trap may be different from the second trap, and sharing some common features.

The electrode 308 (also referred to as the positive electrode) of the second trap 305 may be connected to a positive terminal of a voltage source 318 via a connecting wire 330. Similarly, the electrode 310 (also referred to as the negative electrode) of the second trap may be connected to a measurement device 334 and then to a negative terminal of the same voltage source 318 via a connecting wire 332. A measurement device may not be connected to the first trap 303 but only to the second trap, for example. In some embodiments, a switch (not shown) may be included and a controller (such as controller 12 of FIG. 1) may control the switch to selectively connect and disconnect the electrodes from the voltage source.

The voltage source 318 may supply a lower voltage to the second trap 305 compared to the voltage supplied to the first trap 303. The voltage source 316 may be capable of supplying a voltage between 500 and 2000V (e.g., 1000 V), and the voltage source 318 may be capable of supplying a voltage between 1 and 500 V (e.g., 10 V). These voltages are relative to a gap of about 1 mm, and may be scaled accordingly if a different gap is used so as to maintain a similar electric field.

Thus, a uniform electric field may be generated between the electrodes of the first trap and between the electrodes of the second trap. Further, the first trap may be sufficiently isolated from the second trap so that there is reduced interaction between the two electric fields. As such the uniform electric field generated between the electrodes of the first trap may be stronger than the uniform electric field generated between the electrodes of the second trap. The electric field may function to attract and/or repel charged PM entering the traps. Herein, the voltage sources 316 and 318 may be controlled by a controller, such as controller 12 of FIG. 1, for example.

Similar to PM sensor 201, exhaust may enter the PM sensor 301 via holes 346 (as indicated by arrow 302), and may further travel along the conduits (not shown) arranged inside the PM sensor 301 such that the exhaust enters the first trap 303 as indicated by arrow 307. In some examples, the exhaust entering the first trap may be orthogonal to the flow of exhaust in the exhaust pipe. In some more examples, the traps in the PM sensor may be arranged such that the exhaust entering the first trap may be parallel to the direction of flow of exhaust in the exhaust pipe, without deviating from the scope of the invention. Other arrangements of the traps within the PM sensor may also be envisioned where the exhaust may enter the first trap at other incident angles between 0° and 90° with respect to direction of exhaust flow inside the exhaust pipe.

As such, the PM sensor 301 may include an inner protection tube 341 that may block exhaust from entering the second trap before entering the first trap, for example. Charged PMs or soot 312 in the exhaust may enter the first trap 303 and further enter the space between the positive electrode 304 and the negative electrode 306. When a voltage bias is applied between the electrodes of the first trap 303, a uniform electric field may be generated in the space between the electrodes of the first trap, for example. Due to the uniform electric field existing between the electrodes, charged PM entering the first trap may experience electrostatic forces attracting them towards the electrodes of opposite polarity, for example (indicated by arrow 322). For example, PM carrying a small negative charge may be attracted towards the positive electrode 304 of the first trap, while the PM carrying a small positive charge may be attracted towards the negative electrode 306 of the first trap. Herein, high voltage may be applied to the electrodes of the first trap via the voltage source 316.

The first trap may begin to collect and accumulate the PM entering the first trap. Herein, the PM 312 entering the first trap 303 may begin to form aggregates 313 and 315 (also known as dendrites) on the surfaces of the electrodes of the first trap. Once the aggregates contact the surfaces of the electrodes, they may acquire the same polarity surface charge as the electrode surface as explained earlier.

Briefly aggregate 313 collecting on the positive electrode 304 may acquire a positive surface charge. Similarly, aggregates 315 forming on the negative electrode 306 may acquire a negative surface charge. As explained earlier, the aggregates may experience weak Van der Waals forces that keep the aggregates attached to the surfaces of the electrodes. In addition, due to the transfer of electric charges from the electrodes themselves, the aggregates may begin to possess increased surface charges. When the aggregates 314 reach a threshold size, then the surface charges may reach threshold charge levels such that the electrostatic repulsion from the electrode may begin to be stronger than the weak Van der Waals force attaching them to the electrode. The increased repulsive forces may cause the aggregates 314 to break free from the surfaces of the electrodes and flow out of the first trap. However, when breaking away from the electrodes of the first trap and exiting the first trap, the aggregates still possess their surface charge. Thus, the first trap may be primarily used for accumulating and charging the incoming soot. However, the first trap may not be used to measure soot load on the PM sensor.

As explained earlier, a second trap 305 may be juxtaposed to the first trap. Herein, the second trap is positioned apart from the first trap with only space and no other components there-between. Exhaust flow may carry the aggregates 314 breaking off the electrodes of the first trap into the second trap. Similar to the first trap, the second trap may also include positive and negative electrodes connected to positive and negative terminals of a voltage source 318. Herein, the voltage source 318 supplies a voltage lower than that supplied by the voltage source 316, for example. The second trap may additionally include a measurement device 334. Further, the voltage source 318 and the measurement device of the electrical circuit may be controlled by a controller, such as controller 12 of FIG. 1, so that particulate matter collected at the PM sensor may be used for diagnosing leaks in the DPF, for example. As such, the measurement device 334 may be any device capable of reading a resistance change across the electrodes, such as a voltmeter or ammeter.

Similar to the first trap, a uniform electric field also exists between the electrodes of the second trap. However, the electric field in the second trap is weaker than the first trap, because of the lower voltage that is applied across the electrodes of the second trap. When the aggregates carrying large surface charges enter the second trap 305, they may be quickly attracted towards the electrodes of opposite polarity. As the aggregates 314 get deposited between the positive electrode 308 and the negative electrode 310, the current measured by the measurement device 334 may increase. The controller, such as controller 12 of FIG. 1, may be able to use the current measured by the measurement device 334 and infer a corresponding PM or soot load on the second trap 305 of the PM sensor 301. As such, the second trap 305 may be primarily used only for measuring the soot load on the PM sensor 301 and not for charging the soot, for example. In some examples, the aggregates exiting the first trap and entering the second trap may possess increased surface charges, as a result, larger currents may be detected by the measurement device 334. As a result, in such examples, the detection circuitry may be simplified, and additional amplifiers may not be required. In this way, by positioning the second trap near the exit of the first trap, all of the aggregates escaping out of the first trap may be captured by the second trap, thereby increasing the soot load estimation efficiency of the PM sensor. Herein, the electrodes of the traps are planar and continuous, and not interdigitated. Further, the planar electrodes are positioned parallel to one another, and also parallel to the exhaust flow direction.

The cylindrical electrode structures shown in FIG. 2 and the planar electrodes shown in FIG. 3 are non-limiting example of electrode structure. Other shapes and geometries of the electrodes may also be possible without deviating from the scope of the invention. Some more examples of the electrode structure include wavy or curved structures, textured electrode surfaces, parallel plates or discs, etc.

Figure 4:
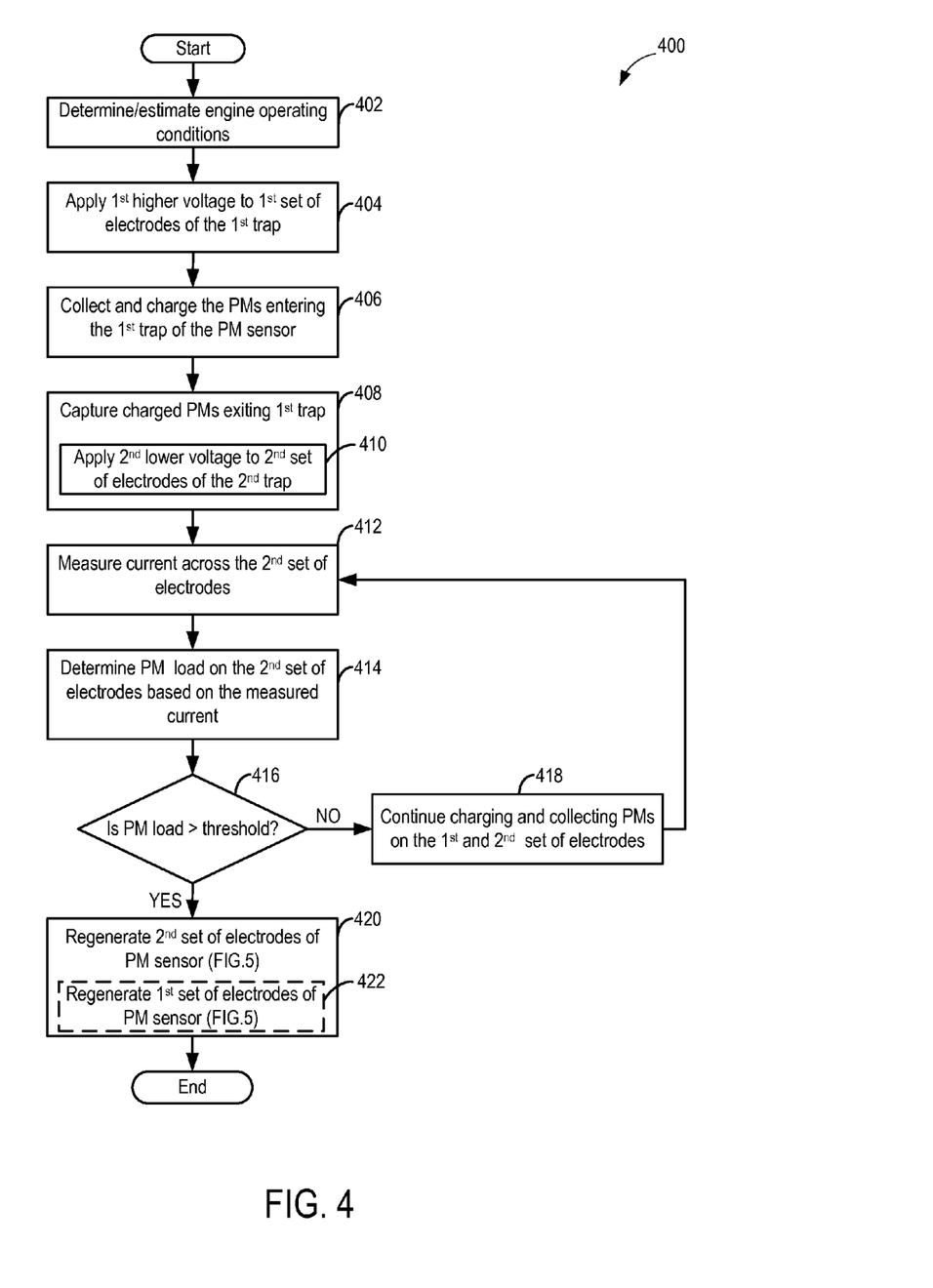
FIG. 4 shows a flow chart depicting a method for charging PM at a first trap and further measuring PM in the exhaust by a second trap, according to the present disclosure.

Turning now to FIG. 4, an example method for charging PM in a first trap of a PM sensor, and measuring the PM load using a second trap located inside the same PM sensor is shown. Specifically, the first trap may be used only for accumulating and charging the incoming PMs in the exhaust, and the second trap may be used only for measuring the soot load of the PM. Instructions for carrying out method 400 and the rest of the methods included herein may be executed by a controller (such as controller 12 shown in FIG. 1 and FIGS. 2 and 3) based on instructions stored on a memory of the controller and in conjunction with signals received from sensors of the engine system, such as the sensors described above with reference to FIGS. 1, 2 and 3. The controller may employ engine actuators of the engine system to adjust engine operation, according to the methods described below.

At 402, method 400 includes determining and/or estimating engine operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

At 404, method 400 includes applying a first higher voltage to the first set of electrodes of first trap. In one example, the first set of electrodes may include cylindrical electrodes connected to positive and negative terminals of a voltage source capable of supplying a higher voltage (as shown in FIG. 2). In a second example, the first set of electrodes may be planar electrodes facing one another and further connected to positive and negative terminals of the voltage source supplying a higher voltage (as shown in FIG. 3).

The controller (such as controller 12 of FIG. 1) may apply the first voltage to the first set of electrodes by turning ON the voltage source (e.g., voltage source 216 of FIG. 2 and voltage source 316 of FIG. 3), connecting the terminals to the electrodes (by closing a switch, for example) and setting the voltage to a first setting wherein a high voltage bias (1000 V, for example) is applied to the electrodes. When the voltage is applied to the electrodes, an electric field is generated between the electrodes which may aid to attract charged PM entering the PM sensor.

Next at 406, method 400 includes collecting the PM and forming aggregates or dendrites across the surface of the electrodes. Furthermore, when the PM get collected on the electrode surface, some of the charge from the electrodes get transferred to the PM themselves, thereby charging the PM. The bias is selected such that natively charged PM is collected (and grows into highly charged dendritic structures or aggregates which can break off), but not so high that broken-off soot structures cannot escape in the desired operating flow regimes. Once they acquire sufficient charge, the PM aggregates may detach from the electrodes, and may exit the first trap.

The charged PM aggregates exiting the first trap may experience an electrostatic attraction towards the second set of electrodes of the second trap, separated from the first trap by a distance. At 408, method includes capturing the charged PMs exiting the first trap. As such, capturing the charged PMs may include applying a second lower voltage to the second set of electrodes of the second trap at 410. Herein, the second trap may further include a measuring circuitry to determine a current across the electrodes (at 412), for example, when the charged PM gets deposited across the electrodes of the second trap. The charge measuring portion of the second trap may include two electrodes with a lower bias (5-50 V, for example) applied, such that charged PM is drawn towards the second set of electrodes but not so high that the PM grows into dendrites which may break off and support their own current amplification. In some examples, electric current on the order of pA to nA may be measured in response to PM load or concentration.

At 414, method 400 includes determining if PM load or soot load on the second set of electrodes of the second trap is greater than a threshold PM load based on the current measured across the electrodes of the second trap. The PM load may be continually inferred and updated based on resistance or conductance changes that occur between the electrodes of the sensor as a result of PM deposition between the second set of electrodes. Next at 416, method includes determining if the PM load on the second set of electrodes is greater than a threshold. In one example, when the PM load on the second trap reaches or exceeds the threshold as measured by conductance across the second set of electrodes of the PM sensor (such as electrodes 208 and 210 shown in FIG. 2, and electrodes 308 and 310 shown in FIG. 3, for example), or when the electrical current measured by measurement device (such as measurement device 234 of FIG. 2, measurement device 334 of FIG. 3, for example) exceeds a threshold, PM sensor regeneration conditions may be considered met. If PM sensor regeneration conditions are met, method 400 proceeds to 420 where the second set of electrodes may be regenerated by initiating a regeneration routine as described in FIG. 5. Regenerating the second set of electrodes of the PM sensor may include heating up the electrodes using heating elements (such as a heating element coupled to the second trap, not shown) until the electrodes of the second trap are burned free of the soot deposited on them. By intermittently regenerating the second trap, it may be returned to a condition more suitable for collecting aggregates. In addition, accurate information pertaining to the exhaust soot level may be inferred from the sensor regeneration and relayed to the controller.

In some examples, the first set of electrodes may also be regenerated by initiating the regeneration routine at 422. For example, the first trap may be regenerated after completion of threshold number of regenerations of the second trap. As such, the first set of electrodes of the PM sensor may be regenerated less frequently than second set of electrodes of the PM sensor, for example, to remove the exhaust PMs collected on the sensor electrodes. In some more examples, both the traps may be alternatingly regenerated, or concurrently regenerated.

In some cases, for a non-leaking DPF for example, the sensor may rarely be regenerated over a drive cycle. Thus, for these conditions, method 400 ends and then starts again going back to 402.

However, if the PM load is lower than the threshold when checked at 416, then method proceeds to 418, where the PMs may be continued to charged and collected on the first set of electrodes and the method returns to 412 where the current across the second set of electrodes is measured as explained earlier. In this way, by using the first trap to charge the incoming PMs and using the second trap to measure the highly charged aggregates exiting the first trap, sensor sensitivity may be increased. In addition, the functioning of the PM sensor to estimate the filtering capabilities of the DPF (and thereby to detect DPF leaks) may be improved and exhaust emissions compliance may be improved as PMs in the exhaust may be detected more accurately and reliably.

Figure 5:
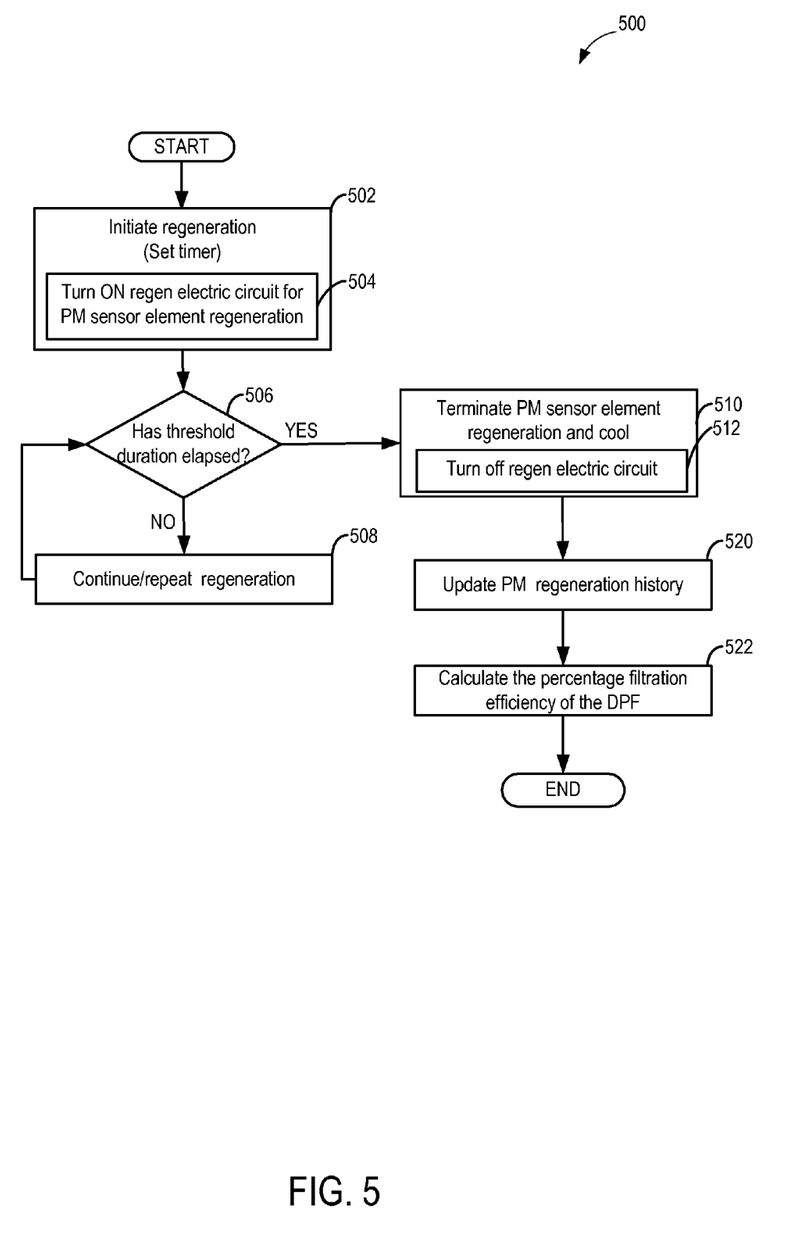
FIG. 5 shows a chart depicting a method for performing regeneration of the PM sensor.

Turning now to FIG. 5, a method 500 for regenerating one or more traps of the PM sensor (such as a PM sensor 106 shown at FIG. 1, PM sensor 201 of FIG. 2 and PM sensor 301 of FIG. 3, for example) is shown. Specifically, when the PM load on the second trap of the PM sensor is greater than the threshold, or when a resistance of the electrodes of the second trap of the PM sensor adjusted for temperature drops to a threshold resistance, the regeneration conditions may be considered met, and the PM sensor may need to be regenerated to enable further PM detection. Herein, the regeneration may be performed on the first set of electrodes of the first trap.

At 502, regeneration of the electrodes of the second trap may be initiated and the second trap may be regenerated by heating up the trap at 504. The PM sensor may be heated by actuating a heating element coupled thermally to the sensor electrode surface, such as a heating element embedded in the sensor, until the soot load of the sensor has been sufficiently reduced by oxidation of the carbon particles between the electrodes. The regeneration is typically controlled by using timers and the timer may be set for a threshold duration at 502. Alternatively, the regeneration may be controlled using a temperature measurement of the sensor tip, or by the control of power to the heater, or any or all of these. When timer is used for regeneration, then method 500 includes checking if the threshold duration has elapsed at 506. If the threshold duration has not elapsed, then method 500 proceeds to 508 where the regeneration may be continued. If threshold duration has elapsed, then method 500 proceeds to 510 where the soot sensor regeneration may be terminated and the electric circuit may be turned off at 512. Further, the electrodes may be cooled to the exhaust temperature for example.

In some examples, the resistance between the electrodes of the second trap (such as the second set of electrodes of the PM sensor) may be measured. From the measured resistance, possibly compensated for temperature, the PM or soot load of the second trap (i.e., the accumulated PMs or soot between the electrodes of the PM sensor) may be calculated. The calculated soot load of the PM sensor may be compared with a threshold. The threshold, may be a lower threshold, lower than the regeneration threshold, for example, indicating that the electrodes are sufficiently clean of soot particles. In one example, the threshold may be a threshold below which regeneration may be terminated. If the soot load continues to be greater than threshold, indicating that further regeneration may be required, regeneration may be repeated. However, if the PM sensor continues to undergo repeated regenerations, the controller may set error codes to indicate that the PM sensor may be degraded or the heating element in the soot sensor may be degraded.

Next at 520, the regeneration history may be updated and stored in memory. For example, a frequency of regeneration and/or an average duration between sensor regenerations may be updated. At 522, various models may then be used by the controller to calculate the percentage efficiency of the DPF the filtration of soot. In this way, the second trap may perform on-board diagnosis of the DPF.

The first set of electrodes of the first trap of the PM sensor may also be regenerated by performing method 500 as described above. However, since the first trap does not include measurement device to determine soot load on the first trap, the controller may regenerate the first trap intermittently. For example, when threshold number of regenerations have been performed on the second trap, the controller may execute method 500 to regenerate the first trap. In some examples, the first trap may be regenerated every time the second trap meets regeneration conditions. In still other examples, the second trap may be regenerated more frequently than the first trap.

Figure 6:
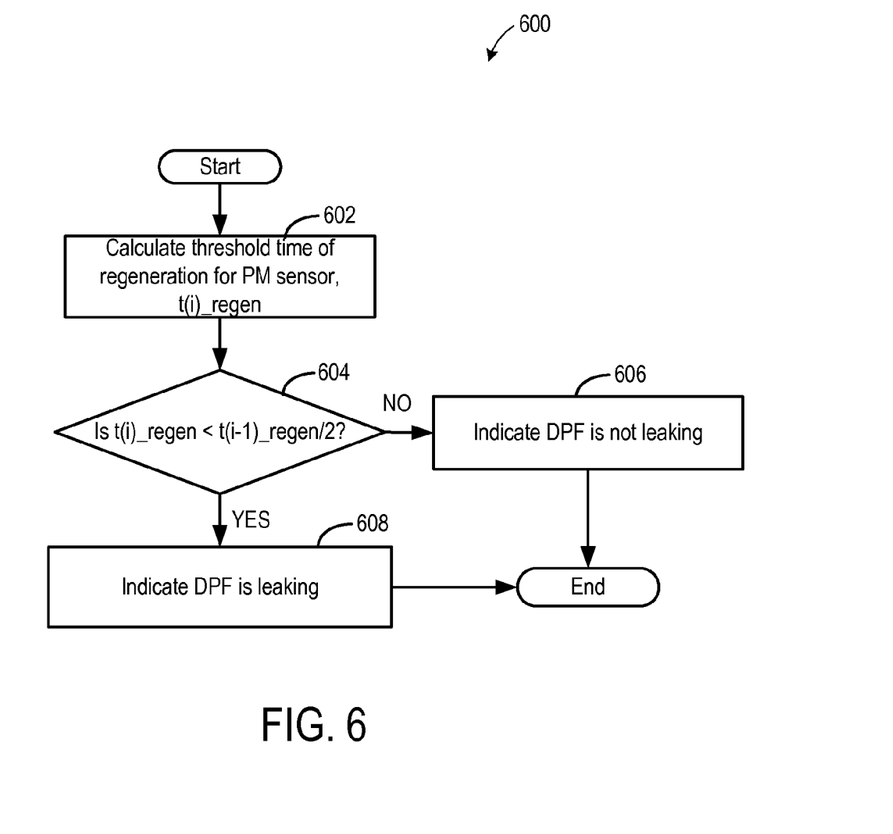
FIG. 6 shows a flow chart depicting a method for diagnosing leaks in a particulate filter positioned upstream of the PM sensor.

FIG. 6 illustrates an example routine 600 for diagnosing DPF function based on the regeneration time of the traps of the PM sensor. At 602, it may be calculated by the controller, through calibration, the time of regeneration for the PM sensor, t(i)_regen, which is the time measured from end of previous regeneration to the start of current regeneration of the PM sensor. Herein, the time of regeneration of the PM sensor may include one or more of the time of regeneration of the first trap and the time of regeneration of the second trap. In some examples, the time of regeneration of the PM sensor may be an average of the time of regenerations of the first trap and the second trap. In still other examples, the time of regeneration of the PM sensor may include the time of regeneration of the second trap only.

At 604, compare t(i)_regen to t(i−1)_regen, which is the previously calibrated time of regeneration of the PM sensor. From this, it may be inferred that the soot sensor may need to cycle through regeneration multiple times in order to diagnose the DPF. If the t(i)_regen is less than half the value of t(i−1) region, then at 608 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code.

A current regeneration time of less than half of the previous regeneration time may indicate that the time for electric circuit to reach the threshold is shorter, and thus the frequency of regeneration is higher. Higher frequency of regeneration in the PM sensor may indicate that the out-flowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change of regeneration time in the soot sensor does not reach threshold t_regen, then at 606 DPF leaking is not indicated. In this way, leaks in a particulate filter positioned upstream of the particulate matter sensor may be detected based on a rate of deposition of the particulates on the particulate matter sensor element.

Figure 7:
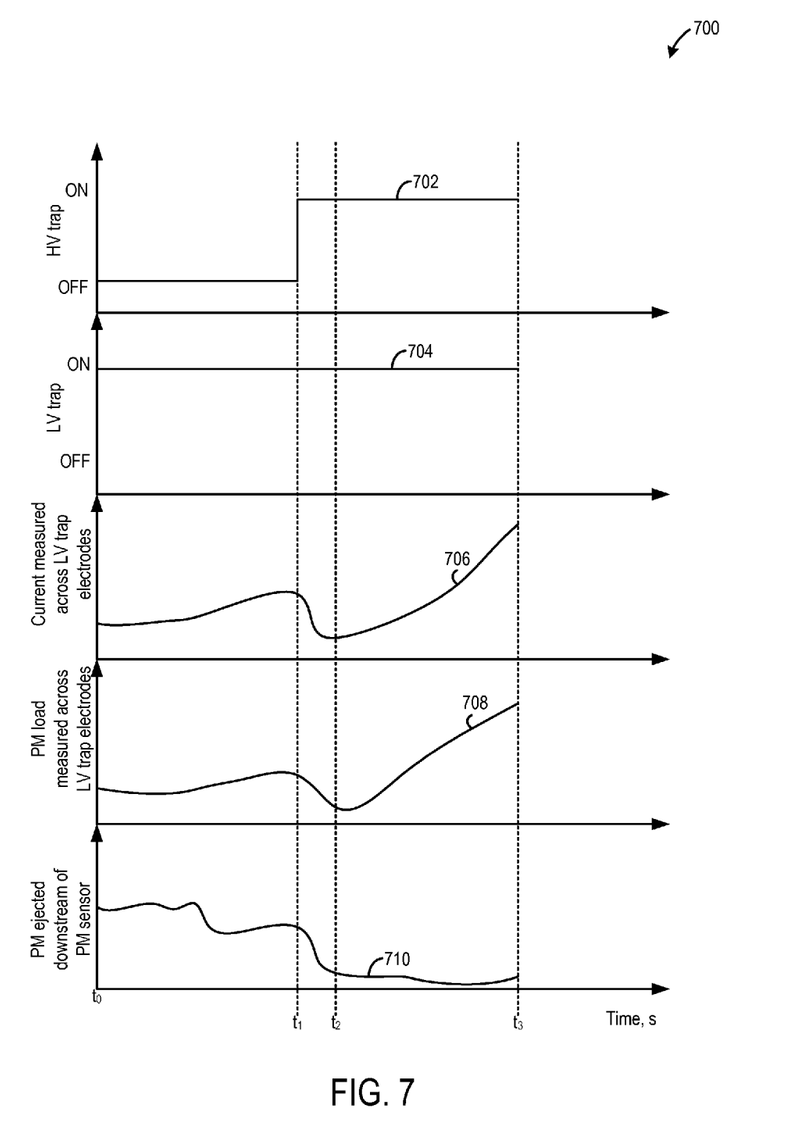
FIG. 7 shows an example relationship between voltages applied to the traps and amount of PM ejected downstream of the PM sensor.

Turning now to FIG. 7, plot 700 shows an example relationship between voltages applied to the first and second traps of the PM sensor and amount of PM ejected downstream of the PM sensor. The first trap wherein higher voltage is applied to the first set of electrodes is referred to as the high voltage (HV) trap and the second trap wherein lower voltage is applied to the second set of electrodes of the second trap is referred to as the low voltage (LV) trap. Plots 702 and 704 show the application of corresponding voltages to the HV and LV trap respectively. Plot 706 shoes the current measured across the LV trap electrodes and plot 708 shows the PM load inferred across the LV trap electrodes based on the current measured across the electrodes of the LV trap. Plot 710 shows the amount of PM ejected downstream of the PM sensor, as measured by a sensor located downstream of the PM sensor with the HV and LV traps. Herein, the downstream soot sensor is included to illustrate the effect of the voltages applied to the HV and LV trap on the PMs exiting the PM sensor. However, the downstream soot sensor may or may not be included in the actual embodiment.

During the time between $t_0$ and $t_1$, the HV trap is OFF (plot 702) and LV trap is ON (plot 704). Herein, turning off the HV trap includes not connecting the electrodes of the HV trap by opening a switch interjected between the electrodes and the high voltage source, for example. In some examples, the controller may set the supply voltage to 0, thereby not applying any considerable voltage between the electrodes of the first trap. However, the LV trap is connected to the voltage source supplying a lower voltage to the second set of electrodes.

As charged PM enters the PM sensor, they may enter the first trap and may not be affected by the electrodes (since the HV trap is OFF) and may directly proceed towards the LV trap. Herein, the surface charge of the PMs entering the PM sensor may not be perturbed. When the PM exits the HV trap, they may encounter the LV trap wherein the electrodes are held at a bias. Though the bias is low and the electric field generated is low, the PM may still undergo electrostatic attraction towards electrodes of the LV trap. Thus, the current measured across the electrodes of the LV trap may increase slightly (plot 706). Correspondingly, there may be slight increase in the PM load on the LV trap (plot 708). A soot sensor placed downstream of the current PM sensor may detect PMs not captured in the LV trap (plot 710).

However, at time $t_1$, the HV trap is turned ON (plot 702). The controller may turn ON the HV trap by closing the switch interjected between the electrodes and the high voltage source, for example. In some examples, the controller may set the supply voltage to 1000 V, thereby applying a high voltage between the electrodes of the HV trap. When the HV trap is turned ON, the natively charged PMs flowing into the HV trap get trapped by the high electric field. The soot deposits into high aspect ratio dendritic structures which are held together via van der waals bonding. The geometry of the dendrites, in combination with the high electric field applied to the accumulation/charging portion may cause charge to accumulate in the dendritic structure.

Immediately after turning ON the HV trap at $t_1$ (plot 702), the PMs entering the PM sensor may begin to accumulate and get charged at the electrodes of the HV trap. During the time between t1 and t2, most of the PMs entering into the PM sensor may be collecting across the electrodes of the HV trap, and the PMs reaching the LV trap downstream of the HV trap may begin to decline. Thus, the current measured across the LV trap electrodes (plot 706) and the corresponding PM load measured across the LV trap (plot 708) may decrease. Further, the amount of PMs ejected out the PM sensor may also drop (plot 710). Thus, the time between $t_1$ and $t_2$, the PMs may be getting accumulated and charged at the HV trap, however, this time may be fairly short for the PM sensor wherein HV trap and LV trap are included.

At $t_2$, the soot dendrites may reach a threshold geometry or height such that the electrical force trapping them on the HV electrodes may exceed the anchoring force, which may then cause the dendrites to break off from the HV trap and carry with them their excess electric charge to the LV trap. The flow through the sensor carries the large, highly charged break-off portion of the dendrite into the charge measurement portion of the sensor, namely the LV trap (which is ON, as shown in plot 704). The relatively lower electric field of the measurement portion of the sensor draws the highly charged dendrite fraction to the electrode wall, where it imparts its charge as seen an increase in the current measured across the electrodes of the LV trap (plot 706). In this way, a real-time measurement of soot concentrations may be determined using the PM sensor using HV and LV traps. In addition, since the LV trap is juxtaposed to the HV trap, the charged dendrites braking off the HV trap may immediately be captured by the LV trap, thereby reducing transient responses to exhaust flow changes.

In this way, as shown between $t_2$ and $t_3$, as more soot is fed into the sensor per unit time, dendrites grow and break off more quickly, thus more charge is delivered to the current measurement portion per unit time, supporting the soot-proportional measurement current. The technical effect of using a HV trap to only charge the incoming soot and further using a LV trap to only measure the charged soot exiting the HV trap, the PM sensor may be able to provide real-time measurements of the soot levels in the exhaust. Further, by using the HV trap to amplify the charge of the PMs, the LV trap may be able to detect larger currents, thereby eliminating need for any amplification circuitry. Furthermore, by including both the HV trap and LV trap within the same PM sensor housing, the soot level measurements may be independent of any changes in exhaust flow rate, for example. Thus, any leaks or degradation of the DPF may be detected more efficiently and effectively.

The systems and methods described above also provide for a method of particulate matter sensing, in an exhaust system, the method comprising collecting and charging particulate matter (PM) in an exhaust entering a PM sensor by applying a first voltage only to a first set of electrodes housed within the PM sensor, and measuring the charged PM by applying a second voltage only to a second set of electrodes housed within the PM sensor further separated from the first set of electrodes by a distance, the first voltage being higher than the second voltage. In a first example of the method, the method may additionally or alternatively include wherein the charging includes transferring charges from the first set of electrodes to PM collected between the first set of electrodes. A second example of the method optionally includes the first example, and further includes wherein the measuring includes attracting the charged PM exiting the first set of electrodes towards the second set of electrodes and depositing the charged PM between the second set of electrodes and determining a soot load of the PM sensor based on an amount of charged PM deposited between the second set of electrodes. A third example of the method optionally includes one or more of the first and the second examples, and further includes regenerating the second set of electrodes when the soot load of the PM sensor is higher than a threshold soot load. A fourth example of the method optionally includes one or more of the first through the third examples, and further includes wherein the first set of electrodes further comprise a first positive electrode connected to a positive terminal of a first voltage source and a first negative electrode connected to a negative terminal of the first voltage source, the first positive electrode separated from the first negative electrode by a first gap, the first voltage source supplying the first voltage. A fifth example of the method optionally includes one or more of the first through the fourth examples, and further includes wherein the second set of electrodes further comprises a second positive electrode connected to a positive terminal of a second voltage source and a second negative electrode connected to a negative terminal of a second voltage source, the first positive electrode separated from the first negative electrode by a second gap, the second voltage source supplying the second voltage. A sixth example of the method optionally includes one or more of the first through the fifth examples, and further includes wherein each of the first positive electrode, the first negative electrode, the second positive electrode, and the second negative electrode comprise of cylindrical electrodes. A seventh example of the method optionally includes one or more of the first through the sixth examples, and further includes wherein the first negative electrode surrounds the first positive electrode, and wherein the second negative electrode surrounds the second positive electrode. An eighth example of the method optionally includes one or more of the first through the seventh examples, and further wherein each of the first positive electrode, the first negative electrode, the second positive electrode, and the second negative electrode comprise of planar electrodes.

The systems and methods described above also provide for a method of particulate matter sensor, comprising applying a first electric field between a first pair of electrodes of a first trap of the PM sensor to accumulate PM entering the first trap to form dendrites, charging the dendrites, and applying a second electric field between a second pair of electrodes of a second trap to capturing the dendrites detaching from and exiting the first trap, the second electric field being lower than the first electric field. In a first example of the method, the method may additionally or alternatively include separating the second trap from the first trap by a distance and further housing the first trap and the second trap within the same PM sensor, the first trap amplifying charge of the dendrites. A second example of the method optionally includes the first example, and further includes wherein the capturing includes depositing the dendrites between the second pair of electrodes of the second trap and generating a current based on the dendrites depositing on the second trap. A third example of the method optionally includes one or more of the first and the second examples, and further includes regenerating the PM sensor when the current generated across the second pair of electrodes exceeds a threshold current. A fourth example of the method optionally includes one or more of the first through the third examples, and further includes wherein the first pair of electrodes and the second pair of electrodes include parallel planar electrodes that are not interdigitated. A fifth example of the method optionally includes one or more of the first through the fourth examples, and further includes wherein the first pair of electrodes and the second pair of electrodes include cylindrical electrodes.

The systems and methods described above also provide for a particulate matter sensor comprising A particulate matter (PM) sensor system, comprising a high voltage (HV) trap including a first pair of electrodes housed within a PM sensor, a low voltage (LV) trap including a second pair of electrodes housed within the PM sensor, the LV trap separated from the HV trap by a distance, and a controller with computer readable instructions stored on non-transitory memory for applying a first voltage only across the first pair of electrodes to charge soot entering the HV trap, and applying a second voltage only across the second pair of electrodes of the LV trap to capture soot exiting the first trap and entering the second trap, the second voltage being lower than the first voltage. In a first example of the particulate matter sensor, the sensor may additionally or alternatively include wherein the controller includes further instructions for determining soot load of the PM sensor based on a current measured across the second pair of electrodes of the LV trap. A second example of the particulate matter sensor optionally includes the first example and further wherein the controller includes further instructions for regenerating the LV trap when the soot load rises above a threshold soot load. A third example of the particulate matter sensor optionally includes one or more of the first and the second examples, and further includes wherein each of the first pair of electrodes and the second pair of electrodes include a positive planar electrode and a negative planar electrode, the positive planar electrode and the negative planar electrode including planar electrodes separated by a distance. A fourth example of the particulate matter sensor optionally includes one or more of the first through the third examples, and further includes wherein each of the first pair of electrodes and the second pair of electrodes include a positive cylindrical electrode and a negative cylindrical electrode, the positive cylindrical electrode separated and surrounding the negative cylindrical electrode.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
    collecting and charging particulate matter (PM) in an exhaust entering a PM sensor by applying a first voltage only to a first set of electrodes housed within the PM sensor; and
    measuring charged PM by applying a second voltage only to a second set of electrodes housed within the PM sensor further separated from the first set of electrodes by a distance, the first voltage being higher than the second voltage, and where a first trap coupled to the first set of electrodes is upstream of a second trap coupled to the second set of electrodes with respect to a direction of exhaust gas flow.

2. The method of claim 1, wherein the charging includes transferring charges from the first set of electrodes to PM collected between the first set of electrodes.

3. The method of claim 1, wherein the measuring includes attracting the charged PM exiting the first set of electrodes towards the second set of electrodes and depositing the charged PM between the second set of electrodes and determining a soot load of the PM sensor based on an amount of charged PM deposited between the second set of electrodes.

4. The method of claim 3, further comprising regenerating the second set of electrodes when the soot load of the PM sensor is higher than a threshold soot load.

5. The method of claim 1, wherein the first set of electrodes further comprises a first positive electrode connected to a positive terminal of a first voltage source and a first negative electrode connected to a negative terminal of the first voltage source, the first positive electrode separated from the first negative electrode by a first gap, the first voltage source supplying the first voltage.

6. The method of claim 5, wherein the second set of electrodes further comprises a second positive electrode connected to a positive terminal of a second voltage source and a second negative electrode connected to a negative terminal of the second voltage source, the second positive electrode separated from the second negative electrode by a second gap, the second voltage source supplying the second voltage.

7. The method of claim 6, wherein each of the first positive electrode, the first negative electrode, the second positive electrode, and the second negative electrode comprises cylindrical electrodes.

8. The method of claim 7, wherein the first negative electrode surrounds the first positive electrode, and wherein the second negative electrode surrounds the second positive electrode.

9. The method of claim 5, wherein each of the first positive electrode, the first negative electrode, the second positive electrode, and the second negative electrode comprises planar electrodes.

10. A method for a particulate matter (PM) sensor, comprising:
    applying a first electric field between a first pair of electrodes of a first trap of the PM sensor to accumulate PM entering the first trap to form dendrites;
    charging the dendrites; and
    applying a second electric field between a second pair of electrodes of a second trap to capture the dendrites detaching from and exiting the first trap, the second electric field being lower than the first electric field, and where the second trap is arranged downstream of the first trap with respect to a direction of exhaust gas flow.

11. The method of claim 10, further comprising separating the second trap from the first trap by a distance and further housing the first trap and the second trap within the same PM sensor, the first trap amplifying charge of the dendrites.

12. The method of claim 10, wherein the capture includes depositing the dendrites between the second pair of electrodes of the second trap and generating a current based on the dendrites depositing on the second trap.

13. The method of claim 12, further comprising regenerating the PM sensor when the current generated across the second pair of electrodes exceeds a threshold current.

14. The method of claim 10, wherein the first pair of electrodes and the second pair of electrodes include parallel planar electrodes that are not interdigitated.

15. The method of claim 10, wherein the first pair of electrodes and the second pair of electrodes include cylindrical electrodes.

16. A particulate matter (PM) sensor system, comprising:
    a high voltage (HV) trap including a first pair of electrodes housed within a PM sensor;
    a low voltage (LV) trap including a second pair of electrodes housed within the PM sensor, the LV trap separated from the HV trap by a distance; and
    a controller with computer readable instructions stored on non-transitory memory for:
        applying a first voltage only across the first pair of electrodes to charge soot entering the HV trap; and
        applying a second voltage only across the second pair of electrodes of the LV trap to capture soot exiting the HV trap and entering the LV trap, the LV trap arranged downstream of the HV trap, the second voltage being lower than the first voltage.

17. The system of claim 16, wherein the controller includes further instructions for:
    determining soot load of the PM sensor based on a current measured across the second pair of electrodes of the LV trap.

18. The system of claim 17, wherein the controller includes further instructions for:
    regenerating the LV trap when the soot load rises above a threshold soot load.

19. The system of claim 16, wherein each of the first pair of electrodes and the second pair of electrodes includes a positive planar electrode and a negative planar electrode, the positive planar electrode and the negative planar electrode including planar electrodes separated by a distance.

20. The system of claim 16, wherein each of the first pair of electrodes and the second pair of electrodes includes a positive cylindrical electrode and a negative cylindrical electrode, the positive cylindrical electrode separated and surrounding the negative cylindrical electrode.

* * * * *